United States Patent
Schweitzer et al.

(10) Patent No.: US 12,216,061 B2
(45) Date of Patent: Feb. 4, 2025

(54) METHOD FOR DETERMINING A PARAMETER DEPENDENT ON THE CONCENTRATION OF AT LEAST ONE ANALYTE IN A SAMPLE LIQUID

(71) Applicant: Endress+Hauser Conducta GmbH+Co. KG, Gerlingen (DE)

(72) Inventors: Daniel Schweitzer, Remshalden (DE); Ulrich Kathe, Ludwigsburg (DE); Michael Ingelmann, Vaihingen/Enz (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 1030 days.

(21) Appl. No.: 17/128,988

(22) Filed: Dec. 21, 2020

(65) Prior Publication Data

US 2021/0190700 A1 Jun. 24, 2021

(30) Foreign Application Priority Data

Dec. 20, 2019 (DE) .................... 10 2019 135 489.7

(51) Int. Cl.
*G01N 21/79* (2006.01)
*G01N 21/80* (2006.01)
*G01N 31/16* (2006.01)
*G01N 33/18* (2006.01)

(52) U.S. Cl.
CPC ............. *G01N 21/79* (2013.01); *G01N 21/80* (2013.01); *G01N 31/16* (2013.01); *G01N 33/1806* (2013.01)

(58) Field of Classification Search
CPC ........ G01N 21/78; G01N 21/79; G01N 21/80; G01N 21/3103; G01N 33/1806; G01N 31/16; G01N 31/162; G01N 31/164
USPC .... 436/84, 145, 149, 150, 163, 164; 422/75, 422/79, 82.05, 82.09
See application file for complete search history.

(56) References Cited

U.S. PATENT DOCUMENTS

| | | | |
|---|---|---|---|
| 4,058,965 A | 11/1977 | Shaw et al. | |
| 7,349,760 B2* | 3/2008 | Wei | G01N 31/162 422/50 |
| 2014/0273244 A1* | 9/2014 | Bolduc | G01N 31/16 436/51 |

FOREIGN PATENT DOCUMENTS

| | | |
|---|---|---|
| CN | 1392409 A | 1/2003 |
| CN | 102753951 A | 10/2012 |
| CN | 104535709 | 4/2015 |

(Continued)

*Primary Examiner* — Maureen Wallenhorst
(74) *Attorney, Agent, or Firm* — Kelly J. Smith; Endress+Hauser (USA) Holding, Inc.

(57) ABSTRACT

A method for determining a parameter includes forming a reaction mixture by adding a volume of a solution to a sample. The solution contains a substance acting as a reaction partner for the analyte, where the reaction partner enters into a chemical reaction with the analyte, forming a reaction product of the analyte. The volume of the solution is adjusted, based on measured values of a physical or chemical measurand which are detected during the addition of the solution in the reaction mixture and whose value depends on the concentration of the analyte or of the substance in the reaction mixture. A titration of the solution to be titrated is subsequently performed from which a quantity of the substance present in the reaction mixture after addition of the volume of the solution is determinable, and a value of the parameter is ascertained using the titration.

13 Claims, 3 Drawing Sheets

(56) References Cited

FOREIGN PATENT DOCUMENTS

| | | | |
|---|---|---|---|
| CN | 104535709 | A | 4/2015 |
| CN | 105102963 | A | 11/2015 |
| CN | 107703202 | A | 2/2018 |
| CN | 107764933 | A | 3/2018 |
| CN | 109444244 | A | 3/2019 |
| CN | 110325504 | A | 10/2019 |
| DE | 259459 | A1 | 8/1988 |
| DE | 19950879 | A1 | 1/2002 |
| FR | 981465 | A | 5/1951 |
| GB | 1421223 | A | 1/1976 |
| WO | 2012055795 | A1 | 5/2012 |
| WO | 2018/166881 | A1 * | 9/2018 |

* cited by examiner

METHOD FOR DETERMINING A PARAMETER DEPENDENT ON THE CONCENTRATION OF AT LEAST ONE ANALYTE IN A SAMPLE LIQUID

CROSS-REFERENCE TO RELATED APPLICATION

The present application is related to and claims the priority benefit of German Patent Application No. 10 2019 135 489.7, filed on Dec. 20, 2019, the entire contents of which are incorporated herein by reference.

TECHNICAL FIELD

The present disclosure relates to a method for determining a parameter which depends on the concentration of at least one analyte in a sample liquid, and to an apparatus for carrying out the method.

BACKGROUND

Titration is a method of quantitative chemical analysis. In this case, an analyte or titrand which is contained in a solution to be titrated in unknown concentration is reacted in a chemical reaction with a reactant, the titrator, which is added to the solution to be titrated in a titration solution containing the titrator in known concentration. The titration solution is added to the solution to be titrated until an effect occurs which can be detected visually or by means of a detection system and which marks the equivalence point of titration. The effect can be, for example, a sudden change of an optical property, such as a color change (for example by an indicator), a sudden change in pH, or a sudden change in the redox potential of the solution to be titrated. The occurrence of this effect is also referred to as an equivalence point. The equivalence point is also referred to as the transition point in titrations in which the attainment of the equivalence point is detectable by a color change. It forms the end point of titration. The concentration of the titrand can be determined from the volume of the titration solution or the amount of the titrator present in the titration solution until the equivalence point is reached.

There are a number of different titration methods, e.g. acid-base titrations, conductivity titrations, precipitation titrations, complexometric titrations or redox titrations. Before the start of the actual titration, it may be necessary to pre-treat the liquid sample, for example by chemical digestion, by adjusting and/or buffering the pH of the sample, by dilution, by addition of an indicator for titration, or by addition of a reactant reacting with the analyte to be determined in the liquid sample in indirect titrations. The solution to be titrated in this way is then titrated by addition of the titration solution.

The type of titration method also determines the type of detection system for determining the titration endpoint. For example, indicator dyes, pH sensors, ion-selective electrodes (ISE), turbidity sensors, conductivity measuring cells or potentiometric redox sensors are used for detecting the equivalence point.

For the automatic performance of titrations, titration apparatuses are known which can be used, for example, in automatic process analyzers. Process analyzers are used for the automated determination of measured variables whose value depends on the concentration of one or more analytes in a generally liquid sample. Such measured variables are, for example, concentrations of certain substances, for example ion concentrations or concentrations of certain chemical molecular compounds, or cumulative parameters such as the chemical oxygen demand (COD) or the permanganate index (PMI). Such process analyzers are used, for example, in the process industry, for example in processes for cleaning or conditioning water, or in the examination and monitoring of water in supply networks or in environmental analysis.

The central element of a titration apparatus is the titration measuring cell. As a rule, it has a titration vessel which captures the solutions involved in titration, as well as a sensor which serves for detecting the transition point. The sensor can be, for example, an electrochemical sensor integrated into the titration vessel and in contact with the solution to be titrated during operation, or an optical sensor. Alternatively, the sensor can also be an optical, for example photometric, sensor arranged outside of the titration vessel, which radiates measurement radiation through a transparent wall or window of the titration vessel through the titration vessel and the solution contained therein.

It is possible to distinguish between direct titrations and indirect titrations. In the case of direct titrations, the analyte whose concentration is the measurand to be determined, or the concentration of which the measurand to be determined depends on, is also the titrand. In the case of indirect titration, the analyte is first reacted in a chemical reaction with a reactant added to the sample in excess. In such an indirect titration, the titrand is the proportion of the reactant still present after complete reaction of the analyte (also referred to as back titration), or a reaction product of the chemical reaction. From the amount of the titrator or the titration solution that has been consumed until the equivalence point is reached, the concentration of the analyte in the sample or a measurand which is dependent thereon, for example a cumulative parameter, can be determined. Indirect titration is carried out, for example, when the reactants react slowly with one another if in principle a (small) excess of a reactant is required, products or intermediates are unstable, or when the chemical equilibrium is too high on the educt side.

A disadvantage of indirect titration processes is, under certain circumstances, a high level of consumption of the solutions used in these processes. This is illustrated in more detail below in an example. The same disadvantages as represented by this example also occur in other indirect titration methods, for example in the case of the standard analytical determination of lime, ammonia or $HgCl_2$.

An example of a common titration method for determining the concentration of oxidizable substances in a liquid is manganometry. An important field of use of manganometry is the determination of the permanganate index (PMI) in water samples, which is a quantitative measure of the oxidizable inorganic and organic substances present in the water. In the measurement of the PMI, the amount of permanganate required for the complete oxidation of the oxidizable inorganic and organic substances present in a sample is determined. The permanganate index is given in mg of oxygen per liter (mg $O_2$/l), a consumption of 4 mg/l $KMnO_4$ corresponding to approx. 1 mg of $O_2$/l for the oxidation of organic substances in water.

There are some standards defining methods for determining the PMI, e. g., DIN ISO 8467, HJ T 100-2003, or GB 11892-89. The methods according to these standards usually contain the following method steps:

1. A sample taken from a sample liquid to be examined is acidified with sulfuric acid.

2. The acidified sample is heated to a target temperature which, depending on the specification, may be up to 100° C.

3. A predetermined volume of a permanganate solution oriented to the measuring range of the method, is added to the acidified sample in a single dose. In order to ensure that all oxidizable substances are oxidized quantitatively, that is to say completely, the amount of added permanganate is such that it is safely present in excess in solution in the reaction mixture prepared from the acidified sample and the permanganate solution, even if the PMI of the sample liquid should lie at the upper end of the measuring range of the process. The violet-colored permanganate is reduced to the colorless divalent $Mn^{2+}$ ion by the oxidizable substances present in the solution.

4. For digestion of the oxidizable substances, the reaction mixture is kept for a specified reaction time, for example 30 min, at a predetermined temperature, for example 100° C., according to the applicable standard. The complete oxidation of the oxidizable substances present in the sample liquid often takes place in a plurality of stages and can be kinetically inhibited; this longer digestion phase is therefore required. Since permanganate was added in excess in the preceding step 3, a still unconsumed proportion of permanganate was present in the reaction mixture at the end of the digestion phase.

5. After digestion, an oxalate solution is added to the reaction mixture, usually likewise in a single dose, wherein the amount of added oxalate is such that oxalate is present in excess with respect to the proportion of permanganate remaining in the reaction mixture after digestion. Oxalate is a powerful reducing agent that reduces the total permanganate not consumed during digestion to $Mn^{2+}$. In order to ensure that even with a low permanganate consumption (at very low concentrations of oxidizable substances) the added oxalate is present in excess of the permanganate, the amount of added oxalate must be the same as the amount of added permanganate in step 3.

6. After the oxalate solution has been added, the solution thus obtained is titrated with a permanganate titration solution, wherein the permanganate as the titrator oxidizing the non-oxidized oxalate portion remains in the solution after step 5 as the titrand. This is therefore a back titration. The titration solution is added either continuously or stepwise or dropwise until the equivalence point of titration is reached. The equivalence point can be determined potentiometrically, either optically, for example photometrically based on the color change of the solution from colorless to violet, or from the redox potential of the solution. From the amount of added permanganate until the equivalence point is reached, the oxalate content originally present in the titrated solution can be concluded, and from this in turn the amount of permanganate consumed in the digestion in step 4. The PMI of the sample can thus be determined from the amount of titrator consumed.

The amount of permanganate solution used in process step 3 and the amount of oxalate solution used in process step 5 are adapted to the measuring range of the process in order to ensure that permanganate or oxalate are in each case present in excess, so that the desired reactions take place completely independently of whether the sample has a PMI lying at the lower or at the upper end of the measuring range. In method step 3, permanganate is therefore added to the acidified sample in a single dose and in a large amount. The consumption of permanganate and oxalate solution is therefore generally high in this method and leads to a systematically often unnecessarily high consumption of reagents in the lower and in the upper measuring range. As a result, this entails high costs for reagents and high disposal costs. If the method is to be carried out in an automatically operating titration or analysis apparatus, correspondingly large reagent storage containers and receptacles for consumption liquid must be made available for the apparatus, and/or the storage containers and receptacles must be changed frequently.

A further disadvantage occurs when permanganate is present in a very high excess relative to the oxidizable substances in the sample, i.e., when the sample has a low PMI. In this case, the digestion in step 4 can form manganese which is very difficult to dissolve, which can lead to poor reproducibility of the analysis results. Manganese precipitation may adversely affect the measurement capability of a sensor used to detect the equivalence point in the back titration.

A disadvantage of the process described above is also that certainty as to whether a sufficient amount of permanganate has been added to the reaction mixture only exists after the end of the digestion phase. The reaction mixture must then still have a violet coloration. If this is not the case, this is an indication that permanganate has been completely consumed during digestion, namely reduced to $Mn^{2+}$, and consequently has not been added in excess in sufficient quantity. In this case, the method is generally terminated and repeated.

At least some of the disadvantages mentioned generally also occur analogously in other back titration methods.

SUMMARY

The object of the present disclosure is therefore to specify an improved method for carrying out indirect titration methods, such as automatically. Advantageously, a reduced consumption of reagents and/or titration solution should be required in this process.

This object is achieved according to the present disclosure by the method according to claim 1. Advantageous embodiments are listed in the dependent claims.

The method according to the present disclosure for determining a parameter dependent on the concentration of at least one analyte in a sample liquid includes providing an optionally pre-treated sample of the sample liquid, e.g. in a titration vessel of a titration measuring cell. Further, the method includes preparing a solution to be titrated from the sample. The preparation includes forming a reaction mixture by adding a volume of a first solution to the sample, where the first solution contains a first substance acting as a reaction partner for the at least one analyte. The reaction partner enters into a chemical reaction with the at least one analyte while forming a reaction product of the at least one analyte. The volume of the first solution is adjusted, such as regulated, on the basis of measured values of a physical or chemical measurand which is detected during the addition of the first solution to the reaction mixture and whose value depends on the concentration of the at least one analyte and/or of the first substance in the reaction mixture.

A titration is subsequently performed of the solution to be titrated from which a quantity of the first substance present in the reaction mixture after addition of the volume of the first solution is determinable. A value of the parameter using the titration is ascertained. By adjusting or regulating the volume of the first solution containing the first substance on the basis of measured values of a physical or chemical measurand whose value depends on the concentration of the at least one analyte and/or of the first substance in the reaction mixture, it is ensured that the total added volume of the first solution is adapted to the originally present value of the parameter to be determined in the sample. Thus, it is unnecessary, out of precaution, to add, irrespective of the value of the parameter actually present in the sample, such a high quantity of the first solution that it would also be sufficient if the actual value of the parameter in the sample were at the upper edge of the measuring range. This considerably reduces the consumption of the solutions involved in the method and also avoids the other disadvantages of the prior art described above.

The volume of the first solution which is added to the sample to form the reaction mixture can advantageously be adjusted, in particular regulated, by means of the measured values detected in the reaction mixture in such a way that the analyte is completely converted by the first substance to the reaction product of the analyte. For this purpose, the volume can be adjusted in such a way that a, preferably small, excess of the first substance relative to the at least one analyte is added to the sample as a whole.

The volume of the first solution added to the reaction mixture per unit of time can be adjusted or regulated on the basis of the measured values detected in the reaction mixture in such a way that the first substance is present in the reaction mixture over a predetermined total time in a preferably low concentration ready for reaction with the at least one analyte. After completion of the addition of the first solution, a preferably small proportion of the first substance which is not converted by the chemical reaction with the at least one analyte then remains in the reaction mixture. The total time may be a digestion phase during which the first substance reacts with the at least one analyte. The total time may be composed of a plurality of individual time segments.

The parameter dependent on the concentration of at least one analyte in the sample liquid can be, for example, an analyte concentration, i.e., a concentration of a single analyte, such as a halide or of hydrogen carbonate (acid capacity), or a cumulative parameter such as the permanganate index or the chemical oxygen demand (COD) of a sample liquid. The value of such a cumulative parameter is influenced by a plurality of different substances which can potentially be present in the sample liquid as analytes. For example, the COD and PMI are a measure for the sum of all oxidizable substances present in the sample liquid. This sample liquid can be water, for example.

Presentation of the sample may comprise measuring a volume of the sample liquid. Optionally, presentation of the sample can also comprise pretreatment steps, such as the dilution of the sample liquid, the addition of an indicator, or the adjustment of a pH of the sample liquid by addition of acid, base or a buffer solution. These optional steps may be performed before or after measuring the volume of the sample liquid.

The first solution can be added to the sample stepwise in individual volume units. The first solution may be added dropwise, for example. Alternatively, the first solution can be continuously transported into the titration vessel at a constantly set or dynamically adjustable dosing rate. In this alternative embodiment, if the first solution is transported through a line into the titration vessel, the dosing rate can be set or regulated, for example, by setting a constant or dynamically adjustable flow rate of the first solution through the line.

The physical or chemical measurand may be, for example, a variable dependent on a coloration of the reaction mixture, a variable dependent on the pH or a particular ion concentration in the reaction mixture, or a redox potential of the reaction mixture. A photometric measurand, for example absorption or extinction of radiation of one or more wavelengths by the reaction mixture, comes into consideration as a variable dependent on a coloration of the reaction mixture.

The measurand can be detected by means of a sensor. The sensor can be, for example, an electrochemical sensor, for example a potentiometric sensor, a conductivity sensor or an optical sensor. A pH sensor or a redox sensor may be used as the potentiometric sensor, for example. A turbidity sensor or a photometric sensor, which serves to measure an absorption or extinction of measuring radiation by a solution contained in the titration vessel, may be considered as an optical sensor. The sensor may be integrated into the titration vessel so that it contacts or dips into a liquid contained in the titration vessel. If the sensor is an optical, e.g., photometric sensor, the sensor can also be arranged at least partially outside of the titration vessel. In this case, the wall of the titration vessel is transparent or has transparent windows for measuring radiation of the sensor, so that a radiation source of the sensor can emit the measurement radiation into the titration vessel and a solution contained therein, and a radiation receiver of the sensor can receive the measurement radiation after passing through the titration vessel and the solution contained therein.

In an advantageous embodiment of the method, during the addition of the first solution to the sample, the measured values of the physical or chemical measurand can be compared with a reference value. During the addition of the first solution, time periods within which the measured values lie above the reference value or time periods within which the measured values lie below the reference value can be detected and added up.

If the physical or chemical measurand determined by means of the sensor is an optical measurand, e.g. absorption, dependent on a coloration of the reaction mixture, it is also possible to record and add up time periods during the addition of the first solution to the sample in which the solution has a specific coloration that can be detected by means of the sensor.

The aforementioned reference value may substantially coincide with a value assumed by the physical or chemical measurand when an equivalence point of the reaction of the first substance with the analyte is reached. For example, the equivalence point of an acid-base reaction is present when a certain amount of acid or base with the equivalent amount of base or acid is in equilibrium in the reaction mixture. If the reaction of the first substance with the analyte is a redox reaction, the Nernst potentials of both half reactions of the redox reaction are identical at the equivalence point. The half reaction in this case means an oxidation of the reducing agent participating in the reaction into its oxidized form (first half-reaction) or a reduction of the oxidizing agent involved in the reaction to its reduced form (second half-reaction).

In that time periods within which measured values lie above the reference value corresponding to the equivalence point, or alternatively time periods within which measured values lie below the reference value corresponding to the equivalence point, are determined and added, the total time can be detected in which one of the reaction partners (analyte or first substance) of the reaction occurring in the reaction mixture, in particular the first substance, was present in a preferably low concentration, which is ready for reaction with the other reaction partner, in particular the at least one analyte. In this way, it is possible to ensure that the first substance is present in the reaction mixture at a sufficient concentration over a desired total period of time and is available in the reaction mixture for the reaction with the proportion of the at least one analyte which has not yet reacted. This is advantageous if reactions of the first substance with the at least one analyte are slow and/or if at least some of the analyte is present in the reaction mixture as a solid and the analyte is digested over a longer period of time.

The step of performing the titration may serve to determine an amount of the first substance present in the reaction mixture after addition of the volume of the first solution.

In a first method variant, the performance of the titration can comprise the following steps:

Addition of a titration solution to the solution to be titrated, wherein said titration solution contains a second substance which forms a chemical reaction as a titrator with a proportion of the first substance which is present as titrand in the solution to be titrated and which is not converted by the chemical reaction with the at least one analyte; and Detection of an equivalence point of titration, e.g. by means of a sensor.

In this method variant, the value of the parameter can be determined from an amount of the titrator and/or the titration solution that is added to the solution to be titrated until the equivalence point is detected. The added amount of the titrator and/or the titration solution corresponds to the equivalent amount of the proportion of the first substance remaining in the reaction mixture after addition of the volume of the first solution, which is not converted by reaction with the at least one analyte, and allows a conclusion to be drawn about the proportion of the first substance converted correspondingly with the at least one analyte and thus about the amount originally present in the sample, e.g. the concentration, of the at least one analyte and correspondingly to the value of the parameter to be determined.

In an alternative second method variant, the production of the solution to be titrated can furthermore comprise the following steps:

After addition of the volume of the first solution to the sample, addition of a volume of a second solution to the sample, wherein the second solution contains a second substance serving as a reaction partner for the first substance, the second solution entering into a chemical reaction with the first substance to form a reaction product of the first substance, and wherein the volume of the second solution is measured such that a proportion of the first substance remaining in the reaction mixture and not converted by the chemical reaction with the at least one analyte is completely converted by the second substance into the reaction product of the first substance.

In order to achieve this complete conversion, the second substance is generally to be added overall in excess relative to the first substance, i.e., after the addition of the second solution, a portion of the second substance which is not converted by the reaction with the first substance is present in the solution to be titrated.

The volume of the second solution can be a fixedly predetermined volume since the previously added quantity or volume of the first solution can be measured on the basis of the measured values of the physical or chemical measurand in such a way that a small, preferably basically known, quantity, e.g. concentration, of the first substance is present in the reaction mixture after completion of the addition of the first solution. In alternative embodiments, it is also possible to adjust or regulate the volume of the second solution in a manner analogous to the volume of the previously added first solution on the basis of measured values of the physical or chemical measurand.

In this second method variant, the titration can be carried out by adding a titration solution to the solution to be titrated, where said solution contains the first substance as a titrator with which the second substance present as a titrand in the solution to be titrated enters into a chemical reaction. An equivalence point of titration is detected, such as by using a sensor.

The value of the parameter can be determined from an amount of the titrator added to the solution to be titrated up to the detection of the equivalence point and/or the titration solution. The amount of the added titrator and/or the titration solution corresponds to the equivalent amount of the proportion of the second substance remaining in the solution to be titrated and not converted by reaction with the first substance, and allows a conclusion to be drawn about the proportion of the first substance correspondingly remaining in the reaction mixture prior to addition of the second solution which was not converted by the chemical reaction with the at least one analyte, and thus the amount of the first substance present in the reaction mixture after addition of the volume of the first solution. This in turn is a measure of the amount or concentration of the at least one analyte originally present in the sample and the parameter to be determined.

The second method variant described here can advantageously be used, for example, if the parameter to be determined is the permanganate index of the sample liquid, which depends on the concentration of oxidizable substances in the sample. In this case, the first substance is permanganate. The volume of the first solution can be adjusted, or regulated, on the basis of measured values of a measurand that is correlated with the concentration of permanganate, in particular a redox potential or a photometric measurement, detected during the addition of the first solution in the reaction mixture. During and after addition of the first solution, the reaction mixture may be heated for a predeterminable time period to accelerate digestion of substances which are difficult to dissolve and/or kinetically inhibited oxidations in the reaction mixture.

In this method embodiment, presentation of the sample can comprise measuring a volume of the sample liquid and adjusting an acidic pH of the sample. This can be done, for example, by adding sulfuric acid to the sample in the titration vessel. Other pre-treatment steps of the sample are conceivable.

In this process variant, the second substance can be oxalate, which reduces permanganate to the colorless $Mn^{2+}$ while forming $CO_2$. Since the volume of the second solution is measured such that the proportion of the first substance remaining in the reaction mixture, i.e., the permanganate in this embodiment, is completely converted by the second substance, here to $Mn^{2+}$, an excess proportion of the added oxalate not converted by reaction with permanganate is present in the solution to be titrated after the addition of the volume of the second solution.

In this embodiment, the titration can be carried out by addition of a titration solution to the solution to be titrated, where the titration solution contains permanganate as a titrator, which oxidizes oxalate present in the solution to be titrated which is not converted by reaction with permanganate, and wherein the equivalence point of titration is detected by means of a photometric sensor or by means of a redox sensor.

As described above, the permanganate index is determined on the basis of the amount of permanganate or titration solution added until the equivalence point to the solution to be titrated is detected.

Advantageously, in all of the method variants and embodiments described herein, one and the same sensor can be used for detecting measurement values of the physical or chemical measurand during the addition of a volume of the first solution to the sample when producing the reaction mixture or the solution to be titrated and for detecting the equivalence point of titration.

The present disclosure also comprises an apparatus for carrying out the method for determining a parameter dependent on the concentration of at least one analyte in a sample liquid according to the above-described method in one or more of the method variants and embodiments described above.

The device includes a titration measuring cell having a titration vessel and a sensor for detecting measured values of a physical or chemical measurand of a liquid contained in the titration vessel. At least one pump is used for transporting and dosing a pre-determinable volume of the sample liquid and liquids to be added to the sample liquid from storage containers into the titration vessel. At least one first storage container contains a first solution to be added to the sample to produce a solution to be titrated and at least one second storage container contains a titration solution for titration of the solution to be titrated.

Fluid conduits and valves are provided, which fluidic connections can be established between the first storage container and the titration vessel, between the second storage container and the titration vessel, and a sample liquid storage container and the titration vessel, in order to transport and dose the solution, the titration solution and/or the sample liquid into the titration vessel using at least one pump. An electronic controller is configured to receive and process measured values of the sensor, to control the at least one pump and the valves for carrying out the method according to one of the above-described embodiments, and to determine values of the parameter on the basis of measured values of the sensor.

BRIEF DESCRIPTION OF THE DRAWINGS

The present disclosure is explained in further detail below on the basis of the exemplary embodiments shown in the figures. The following are shown.

DETAILED DESCRIPTION

Figure 1:
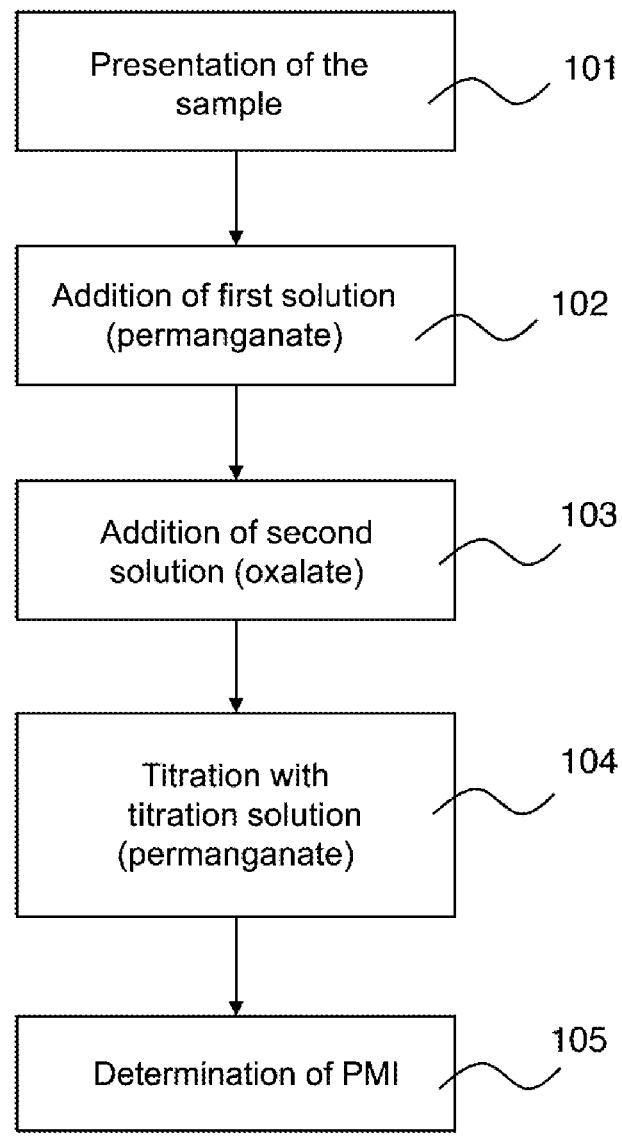
FIG. 1 shows a flow chart of a method for determining the PMI of a sample liquid.

FIG. 1 schematically shows a flow chart for a method for determining the permanganate index PMI of a sample liquid, for example water, by means of a redox titration. The method comprises at least five steps 101-105:

In a first step 101 the sample is initially presented, for example in a titration measuring cell. The titration measuring cell may be part of an automatic analyzer. In the present embodiment, the presentation of the sample includes the measurement of a specific volume of the sample liquid, for example by removing the specific volume from a sample receiver containing the sample liquid. Furthermore, the presentation of the sample may optionally include diluting the volume of the sample liquid by adding a dilution liquid, e.g. distilled water. In the embodiment described herein, the presentation of the sample also comprises adjusting an acidic pH of the sample by adding sulfuric acid to the measured volume of sample liquid.

In a second method step 102, the presented sample is heated, and a first solution containing permanganate in a predetermined or known concentration is added to the presented sample in order to basically completely oxidize the oxidizable substances contained in the sample. Unlike the methods known in the prior art, the first solution is not added in excess in a single dose, but rather over a longer period of time, wherein the total volume added during the second process step is adjusted or regulated on the basis of measured values of a measurand representative of the concentration of permanganate in the reaction mixture formed by the first solution and the sample. During the addition of the first solution, the reaction mixture is stirred and regulated to a fixed temperature value between 80 and 100° C.

The first solution can be added either in portions in individual volume units, for example dropwise, or continuously over a prolonged period of time, for example at a dosing rate of 0.1 ml/min up to a few ml/min. The dosing rate can be varied during the addition. In the present example, the solution is added dropwise. In the present example, the redox potential of the reaction mixture is used as a measurand for the adjustment or regulation of the added volume of the first solution. This can be measured with a potentiometric redox sensor. In an alternative embodiment, absorption or extinction of measurement radiation radiated by the reaction mixture can serve as a measurand for the adjustment of the volume of the first solution added, since the concentration of permanganate in the reaction mixture can be detected well photometrically on account of its intensive violet color.

Oxidizable substances are digested in the sample by the permanganate added to the sample and thereby reduce permanganate to the colorless, divalent $Mn^{2+}$ ion. In part, reactions or subsequent reactions with the oxidizable substances can be slow or kinetically inhibited. If the oxidizable substances are present in part as solids in the sample and in the reaction mixture formed therefrom, their dissolution can also play a role. After addition of a portion, for example one or more drops, of the permanganate solution, permanganate can initially be present in a typically low concentration in the reaction mixture ready for reaction with the oxidizable substances. After a certain time period, all permanganate is consumed. In the case of a portion-wise addition of the first solution, time periods in which permanganate, preferably in low concentration, is present in the reaction mixture can thus alternate with time periods in which the added permanganate is completely consumed by the reaction with the oxidizable substances in the sample. This can be detected by means of the redox sensor or by means of a photometric measurement, for example by the redox potential measured in the reaction mixture falling below a reference value, or by the absorption or extinction of the mixture changing due to the de-colorization of the solution. Once it is determined from the measured values of the sensor that the most recently added permanganate has been consumed, a further portion of the first solution is added, and a further period of time begins in which unreduced permanganate is present in the reaction mixture. It is of course possible initially to dose a first volume of the first solution into the reaction mixture at a higher rate and to continue the addition in portions only thereafter in the manner described. This can be advantageous for accelerating the method if the sample liquid is to be expected to have a high PMI.

The permanganate solution is added in such a way that unreduced permanganate is present in the reaction mixture at least over one or more time periods of the addition in portions.

The mentioned reference value of the measurand that is monitored by the sensor can be determined, for example, in such a way that, when a concentration of permanganate is present for the reaction, the value of the measurand, e.g. the redox potential, lies above the reference value and lies below the reference value given complete consumption (i.e., a concentration that is no longer detectable) of the permanganate. Accordingly, it can be detected photometrically whether the reaction mixture has a violet coloration due to a sufficiently high proportion of permanganate.

If in this way, on the basis of the currently detected measured values, a concentration is detected of permanganate present for the reaction in the solution of the reaction mixture, the addition of the first solution can be slowed down or interrupted until the measured values have fallen below the reference value again, or the reaction mixture no longer has coloration. A further volume unit of the first solution can then be added. The time periods in which unreduced permanganate is present in the reaction mixture can be detected and added up until the sum of the periods in which unreduced permanganate has been present in the reaction mixture is equal to or more than a predetermined value, for example, more than 30 min. The second method step 102 is then ended. This total time forms a digestion phase, while the permanganate present in the solution is available for the oxidation of the oxidizable substances.

Alternatively, it is also possible to continue the addition of the first solution until the detected measured values indicate a permanently present concentration of unreduced permanganate, for example a permanently sustained violet coloration of the solution over a predetermined time period, for example 30 min, or a redox potential of the reaction mixture permanently above the reference value. After this concentration of permanganate has persisted for the predetermined time period, for example after 30 min, the second method step 102 can be terminated.

By adjusting or regulating the volume of the first solution added to the sample on the basis of measured values of the redox potential or on the basis of the coloration of the reaction mixture, it is ensured that overall only a small excess of permanganate is added to the sample. Accordingly, in the second method step 102 modified in this way compared with the conventional method for determining the PMI, a considerable amount of permanganate solution can be saved in samples having a PMI in the region of the lower limit of the measuring range. The problem described above of manganese dioxide formation with too great an excess of permanganate in the reaction mixture is thus also minimized.

In a subsequent third method step 103, a second solution is added to the reaction mixture which contains oxalate as a reaction partner for the proportion of the permanganate remaining in the reaction mixture after completion of the second method step. In the embodiment described here, a fixedly predetermined amount of oxalate or a fixedly predetermined volume is added to the second solution, which can be measured such that the oxalate is present in excess with respect to the proportion of unreacted permanganate present in the reaction mixture. Since in the second method step 102, however, by adjusting the added volume of the first solution based on the measured values of the redox potential, only a comparatively small excess of permanganate has been added and, in comparison to the prior art, hardly fluctuating excess of permanganate was added, the required amount of oxalate is likewise small, so that a considerable amount of the second solution can also be saved in the third method step 103 compared to the method known from the prior art.

The excess oxalate completely reduces the permanganate present in the solution to $Mn^{2+}$, i.e., the solution de-colorizes and the redox potential drops to a value below the reference value. Instead of adding a fixedly predetermined volume of the second solution to the reaction mixture, the volume of the second solution added to the reaction mixture can therefore also be set or regulated in the third method step 103 on the basis of the measured values of the redox potential.

In a subsequent fourth method step 104, a titration of the solution to be titrated obtained in the third method step 103 is titrated with a permanganate titration solution. The first solution added in the first process step can serve as the titration solution, but it is also possible to use different solutions for the two process steps. The permanganate contained in the titration solution reduces the proportion of oxalate still present in the solution to be titrated with the formation of $CO_2$ and $Mn^{2+}$.

The equivalence point of the redox titration can be determined on the basis of the measurement of the redox potential or from the coloration of the solution, for example by a photometric measurement. When the reference value of the redox potential is exceeded, the end of the titration is reached. Alternatively, it is also possible to determine the end point of the titration by detecting a sudden change in the redox potential, or by determining an inflection point of the curve of the measured values of the redox potential (titration curve). The equivalence point can alternatively also be determined by means of a photometric measurement on the basis of a color change of the solution.

From the amount of permanganate added until the equivalence point or titration end point is reached, conclusions can be drawn about the PMI originally present in the sample. This is done in a fifth step. From the amount of permanganate added up to the titration end point, the amount of oxalate present in the solution to be titrated can be determined. This results in the unreacted amount of permanganate present in the reaction mixture after completion of process step 102, including the known amount of added oxalate in process step 103. From this, the value of the PMI of the original sample can be determined given the knowledge of the total amount of permanganate added in process step 102.

The entire method can be carried out in a titration measuring cell in which the redox sensor is integrated. Alternatively, a photometric sensor can be provided which is set up to radiate measuring radiation through the titration vessel 7 and liquid contained therein and to detect measurement signals dependent on an extinction or absorption of the measuring radiation in the liquid. It is also possible for the fourth step 104, that is, titration with the titration solution, to be carried out in a titration measuring cell with an integrated redox sensor or alternatively with a photometric sensor which detects an extinction or absorption of measuring radiation in the liquid to be titrated, while the method steps 101, 102, and possibly also 103 are carried out in a reaction cell upstream of the titration measuring cell.

With particularly high requirements for short analysis times but lower requirements for the measurement accuracy, e.g. in the event that it is only to be monitored whether the PMI of a sample exceeds a predetermined limit value, the method can be terminated after the second step and the PMI can be determined from the volume of the first solution adjusted to the measured values and added to the sample, and the concentration of permanganate in the first solution. At this point in the method, the oxidizable ingredients of the sample are substantially reacted with only a small excess of permanganate present. If the limit value is also maintained with this excess, it can be assumed that the sample does not exceed the limit value.

In the following, two comparative examples are considered according to the conventional method described in the introduction according to the stated standards and two embodiments of a method according to the present disclosure, and the respective consumption of reagents.

In a first comparative example in which the PMI is determined by means of the conventional method, the sample has a PMI of 20 mg $O_2$/l. This is a value close to the upper end of the measuring range of the method. The sample has a volume of 100 ml. It is acidified in a first step and heated to 80° C. Then in a single dose, a first volume V1 of 11 ml of a 0.005 M $KMnO_4$ solution is added to the sample. The reaction mixture obtained in this manner is stirred at 80° C. for 30 min. The color of the reaction mixture remains continuously violet during this time, i.e., $MnO_4^-$ is present throughout the reaction mixture. A second volume V2 of 11 ml of a 0.0125 M $Na_2C_2O_4$ solution is added to the reaction mixture. The solution thus obtained is decolorized because all of the $MnO_4^-$ present in the reaction mixture is reduced to $Mn^{2+}$. The resulting solution is titrated with 0.005 M $KMnO_4^-$ solution to the equivalence point. A third volume V3 of 10 ml of the $KMnO_4^-$ solution is required until the equivalence point is reached.

In a second comparative example in which the PMI is determined entirely analogously to the first comparative example, the sample has a PMI of 0 mg $O_2$/l. This value corresponds to the lower end of the measuring range. The sample again has a volume of 100 ml. All method steps are carried out as in the first comparative example. The $KMnO_4$ solution used for this purpose and $Na_2C_2O_4$ solution have the same concentrations as the corresponding solutions in the first comparative example. The required first volume V1 of the $KMnO_4$ solution is 11 ml, as in the first comparative example, since it is fixedly predetermined by the conventional method and is oriented to the measuring range limits. The required second volume V2 of the $Na_2C_2O_4$ solution is likewise 11 ml. The volume V3 of the $KMnO_4$ solution required for the back titration to the equivalence point is only 0.01 ml.

In a first embodiment of the present disclosure in which the PMI is determined according to the method described with reference to FIG. 1, the sample has a PMI of 20 mg $O_2$/l. First, the sample, which has a volume of 100 ml, is acidified and heated to 80° C. A 0.005 M $KMnO_4$ solution is then added to the sample in portions, and measured values of the redox potential are recorded during the addition. The added volume is adjusted on the basis of the measured values in such a way that the redox potential is above a predetermined reference value over a period of at least 30 min at 80° C., which is selected such that a value of the redox potential lying above the reference value corresponds to the presence of a low permanganate concentration in the reaction mixture ready for reaction with oxidizable substances in the reaction mixture. The solution obtained in this manner is colored violet. In this case, a first volume V1 of the $KMnO_4$ solution of 10.10 ml is required. A fixedly predetermined volume V2 of 0.3 ml of a 0.0125 M $Na_2C_2O_4$ solution is then added to the reaction mixture. The solution thus obtained decolorizes correspondingly on account of the reduction in the total $MnO_4^-$-present in the reaction mixture. The resulting solution is titrated with the 0.005 m $KMnO_4$ solution until the equivalence point is reached. In this case, a third volume V3 of 0.22 ml of the $KMnO_4$ solution is consumed.

In a second embodiment of the present disclosure in which the PMI is determined according to the same method as in the first embodiment of the present disclosure, the sample has a volume of 100 ml and a PMI of 0 mg of $O_2$/l. All method steps are carried out as in the first embodiment. The solutions used have the same concentrations as the corresponding solutions in the first embodiment. The required first volume V1 of the $KMnO_4$ solution is only 0.1 ml, since the detected measured values of the redox potential are permanently above the predetermined reference value over a period of 30 min at 80° C. even after addition of this small volume. The required second volume V2 of the $Na_2C_2O_4$ solution is 0.3 ml, as in the first embodiment. The volume V3 of the $KMnO_4$ solution required for the back titration to the equivalence point is 0.22 ml.

In summary, the total reagent consumption summarized in Table 1 below results in the two comparative examples and the two embodiments:

TABLE 1

| Reagent | Conventional method | | Improved method | |
| --- | --- | --- | --- | --- |
| | Comparative example 1 PMI 20 mg $O_2$/l | Comparative example 2 PMI 0 mg $O_2$/l | Embodiment 1 PMI 20 mg $O_2$/l | Embodiment 2 PMI 0 mg $O_2$/l |
| $KMnO_4$ solution | 21 ml | 11 ml | 10.3 ml | 0.3 ml |
| $Na_2C_2O_4$ solution | 11 ml | 11 ml | 0.3 ml | 0.3 ml |

As a result, it can thus be seen that the method according to the present disclosure manages with considerably lower reagent volumes per measurement.

Figure 2:
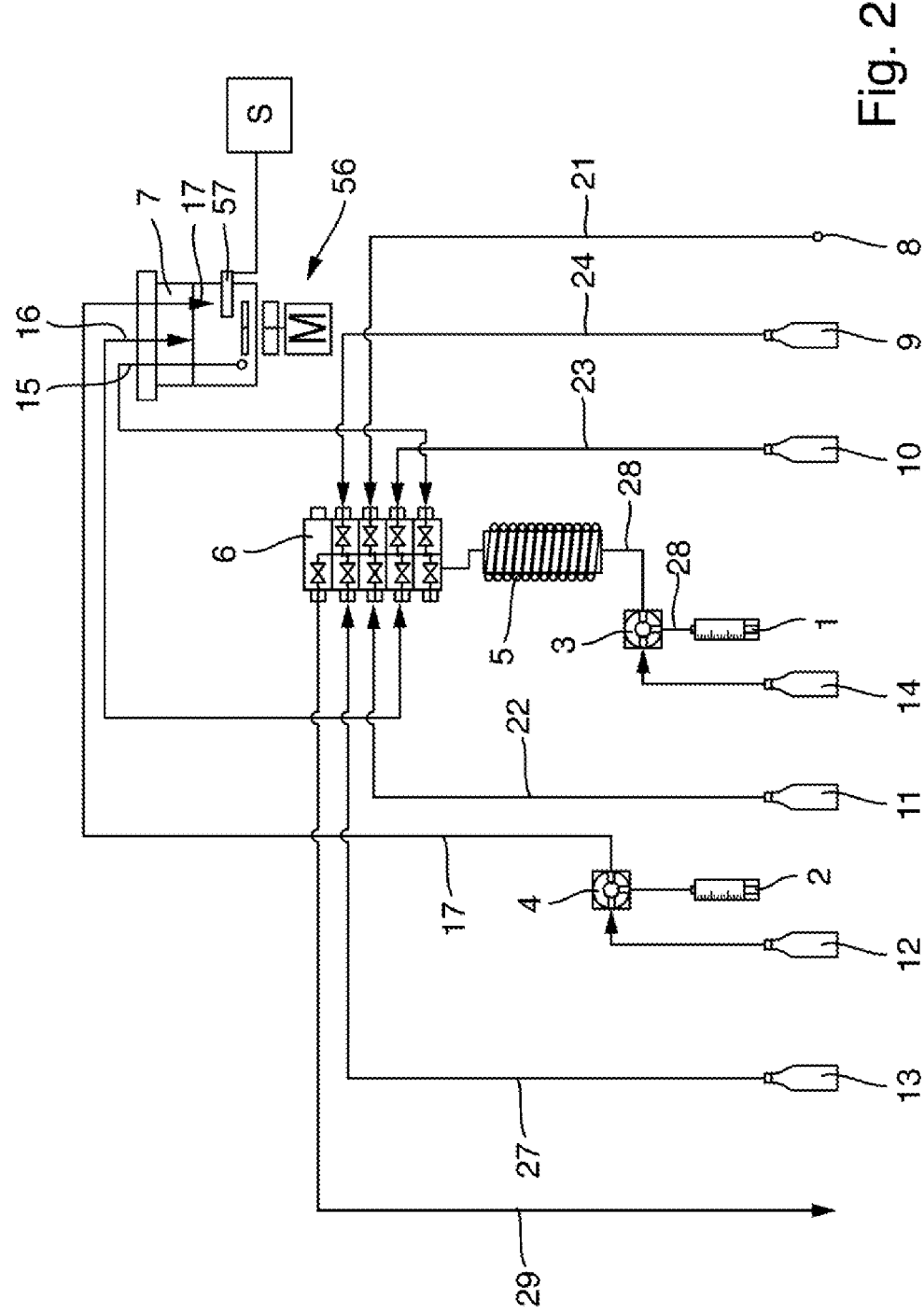
FIG. 2 shows a schematic representation of an analyzer comprising a titration apparatus for determining the PMI of a fluid sample with the method illustrated in FIG. 1.

FIG. 2 shows an apparatus by means of which the above-described method can be carried out in an automated manner. The apparatus is an automatic analyzer for determining a PMI of a sample liquid comprising a titration apparatus.

The analyzer has a titration measuring cell in which a titration vessel 7 is formed. The titration measuring cell also comprises a magnetic stirring unit 56, which is designed to stir a solution contained in the titration vessel 7, and a heater, not shown in FIG. 2, for heating liquid contained in the titration vessel 7. Furthermore, the titration measuring cell may have a sensor 57 configured to detect a physical or chemical measurand of the liquid contained in the titration vessel 7. By means of the sensor 57, it is possible to determine the attainment of the titration end point in an automated manner. In the present embodiment, the sensor 57 is a potentiometric redox sensor. In an alternative embodiment, which is also suitable for determining the PMI of a liquid sample, the sensor can be a photometric sensor which is designed to measure the absorption or extinction of measurement radiation radiated through transparent wall regions of the titration vessel 7 by the liquid contained in the titration vessel 7. In the present example, the sensor 57 is connected to a controller S which controls the titration apparatus and which is set up to receive and process measured values of the sensor 57.

The analyzer has a first storage container 9 with a dilution liquid, for example water, a second storage container 10 with a first reagent, here sulfuric acid, and a third storage container 11 with a second reagent, here an oxalate solution. Furthermore, it comprises a fourth storage container 12 in which the permanganate-containing solution is contained, and a fifth storage container 13 in which a standard solution for the calibration or adjustment of the analyzer is contained.

In order to convey and dose the sample, the dilution liquid, the reagents and the standard solution, the titration apparatus has a first pump 1 which is designed here as a reciprocating pump in the form of a syringe. Instead of a syringe, other pumps can also be used, for example peristaltic pumps or other types of pumps. For the alternating fluidic connection of the first pump 1 to the corresponding storage containers, a central valve device 6 is used in which a plurality of valves is formed. The storage containers 9, 10, 11 and 13 are connected to the valve device 6 via fluid lines 22, 23, 24, 27. The first pump 1 can thus serve to convey and dose all liquids present in these containers into the titration vessel 7. The individual valves of the valve device 6 are closed in the normal state ("normally closed"), i.e., when one of the valves for producing a fluid connection between the first pump 1 and the fluid line connected to the valve is opened, the other valves of the valve device remain in the closed state insofar as they are not activated actively and thus opened, and block fluid transport through all other fluid lines. The valve device 6 can in principle also be a multi-port rotary valve with a common port and a plurality of further ports that are closed in a normal state ("normally closed"). All the fluid lines are formed by plastic hoses in the embodiment described here.

A liquid storage container 8 containing the sample liquid, e.g. a process container from which the liquid can be removed, or a sample storage container, is connected to the valve device 6 via a first fluid line 21. The valve device 6 is also connected to a second fluid line 16 which opens into the titration vessel 7. This second fluid line 16 serves primarily for supplying liquids by means of the first pump 1 via the valve device 6 into the titration vessel 7. It opens into an upper region of the titration vessel 7 which is generally arranged above the liquid level during operation of the device. In the embodiment described here, the first pump 1 can therefore also suck in air via the second fluid line 16 and the valve device 6. In an alternative embodiment, however, for this purpose the first pump 1 can also be connected to an additional air intake line or an air intake opening, which in this case does not necessarily have to open into the titration vessel 7.

In a liquid path between the first pump 1 and the valve device 6, an intermediate storage 5 is arranged, which is formed by a long fluid line. The intermediate storage 5 can be configured, for example, as a hose or as a pipe. It can run in a spiral shape in a space-saving manner, as in the example shown here. The inner diameter of the fluid line forming the intermediate storage 5 can be between 0.5 mm and 3.2 mm, inclusively. The remaining fluid lines designed as tubes can have similar internal diameters, for example between 0.8 mm and 1.6 mm.

The intermediate storage 5 can be fluidically connected to the first pump 1 via a third fluid line 28. Arranged in the third fluid line 28 is a first valve 3 which is configured here as a 3/2 directional control valve and which can selectively block liquid transport by means of the first pump 1 through the third fluid line 28 into the intermediate storage 5 (first position of the valve 3) or release it (second position of the valve 3). The first valve 3 is also connected to a sixth storage container 14 in order to fluidly connect the first pump 1 to the sixth storage container 14 via the section of the third fluid line 28 adjacent to the first pump 1 in the first position of the valve. In the second position, fluid transport from the sixth storage container 14 into the first pump is blocked. The sixth storage container 14 contains a working liquid which behaves indifferently with respect to the titration to be carried out with the titration apparatus, i.e., does not influence the result of titration. In the example described here, the working liquid can be distilled water, for example. With the first pump 1, working liquid can be removed from the sixth storage container 14 and transported into the fluid line 28 and the intermediate storage 5. Via the working liquid present in the fluid line 28 and the intermediate storage 5, the first pump 1 is hydraulically coupled to the liquids transported via the valve device 6 and the fluid lines 21, 22, 23, 24, 27 from the storage containers 9, 10, 11, and 13 so that these liquids do not reach the first pump 1. Entrainment effects due to the transport and dosing of a plurality of liquids by means of the common first pump 1 are thus avoided or at least significantly reduced.

The first pump 1, configured as a syringe, has a cylinder and a piston movable in the cylinder. Through the piston movement, a cavity enclosed by the cylinder, which is connected to the third fluid line 28 via an inlet opening, can be enlarged or reduced in order to draw a liquid into the cavity via the inlet opening or to push it out of the cavity. In an extended end position of the piston, the cavity has a maximum volume; in a retracted end position of the piston, the cavity has a minimum volume. The cavity and at least one section of the third fluid line 28 which adjoins the first pump 1 via the inlet opening are filled with the working liquid during operation. Advantageously, the volume of the working fluid is measured such that, in the retracted end position of the piston, the entire fluid path from the inlet opening of the syringe via the third fluid line 28 and the intermediate storage 5 to the valve device 6 is completely filled by the working liquid. In any case, the volume of the working liquid should be at least as great as the volume that can be received by the syringe, advantageously greater than this, so that it is ensured that no other liquid except for the working liquid enters the syringe or the cavity in the syringe when the apparatus is in operation.

A fourth fluid line 17 connects the titration vessel 7 to a second pump 2 via a second valve 4, which is likewise configured as a 3/2 directional control valve. This is likewise configured as a syringe in the present example. The second valve 4 is also connected to the fourth storage container 12 containing the titration solution. In a first position, it can fluidically connect the fourth storage container 12 to the second pump 2 and temporarily block the fourth fluid line 17 for fluid transport. In a second position, it can fluidically connect the second pump 2 to the titration vessel 7 via the fourth fluid line 17 and at the same time block a transport of liquid from the fourth storage container 12 in the direction of the second pump 2. The second pump 2 is used exclusively for the transport and for the dosing of titration solution into the titration vessel 7.

From the valve device 6, a fifth fluid line 29 leads to a collecting container for spent liquids (not shown in FIG. 2). A discharge line 15 opening into the lower region of the titration vessel 7 can be connected to the first pump 1 via the valve device 6. In this way, the first pump 1 can serve to draw off spent liquid from the titration vessel 7. The first pump 1 can then be fluidically connected to the fifth fluid line 29 via the valve device 6 in order to transport the drawn-in spent fluids into the spent fluids collecting container.

The controller S of the titration apparatus can be a computer, a transducer, a programmable logic controller or some other data processing device. In the present example, it is connected to the valve device 6, the first and second valves 3, 4, as well as the first and second pumps 1, 2, and is designed to control them in order to carry out the method described above with reference to FIG. 1 for determining the permanganate index PMI of the sample taken from the liquid storage container 8. The corresponding communication connections between the controller S and the individual parts of the titration apparatus are not drawn in FIG. 2 for the sake of clarity. In alternative embodiments, the controller S can be configured accordingly for performing other titration methods for determining other parameters of a sample. It may comprise one or more operating programs which serve for the corresponding control of the titration apparatus for carrying out the method and which are set up to execute these operating programs.

To carry out the first method step 101, the controller S controls the first pump 1, the first valve 3, and the valve device 6 for dosing a predefined volume of the sample liquid from the liquid storage container 8 into the titration vessel 7. It then controls the valve device 6 and the first valve 3 for transporting sulfuric acid from the second storage container 10 into the titration measuring cell for acidifying the sample. By means of the heating device, the sample in the titration vessel 7 is heated to a temperature of 80° C.

In order to carry out the second method step 102, the controller S controls the second pump 2, the second valve 4, and the valve device 6 for transporting titration solution from the fourth storage container 12 into the titration vessel 7. The dosing of the volume added into the titration vessel 7 takes place, as described above, on the basis of the measured values of the redox potential provided by the sensor 56 of the controller S. Based on these measured values, the controller S controls the second pump 2 in accordance with the method described above in such a way that a low concentration of permanganate ready for reaction with the oxidizable substances in the sample is present in the solution of the reaction mixture at least over a total period of 30 min. During the execution of the second method step, the temperature of the reaction mixture is continuously maintained at a temperature of 80° C. by means of the heating device.

To carry out the third method step 103, the controller S controls the first pump 1, the first valve 3, and the valve device 6 for transporting a predetermined volume of oxalate solution from the third storage container into the titration vessel 7.

In order to carry out the fourth method step 104, the controller S controls the second pump 2, the second valve 4, and the valve device for the slow or incremental transport of titration solution from the fourth storage container 12 into the titration vessel 7. In order to detect the equivalence point of titration, the controller S evaluates the curve of the measured values of the sensor 56 occurring during the transport of the titration solution into the titration vessel 7. An inflection point of the measured value curve and/or an exceeding of a predetermined reference value of the redox potential indicates the equivalence point of titration. The controller S ends the titration after reaching the equivalence point.

The controller is further set up to determine and output the PMI of the sample in a fifth method step 105 as described above on the basis of the volume of the titration solution consumed during titration, the volume of the oxalate solution added in the third method step, and the volume of the titration solution added in the second method step.

In order to implement the functions described here, the controller S can comprise an evaluation and operating program and be set up to execute these programs.

Figure 3:
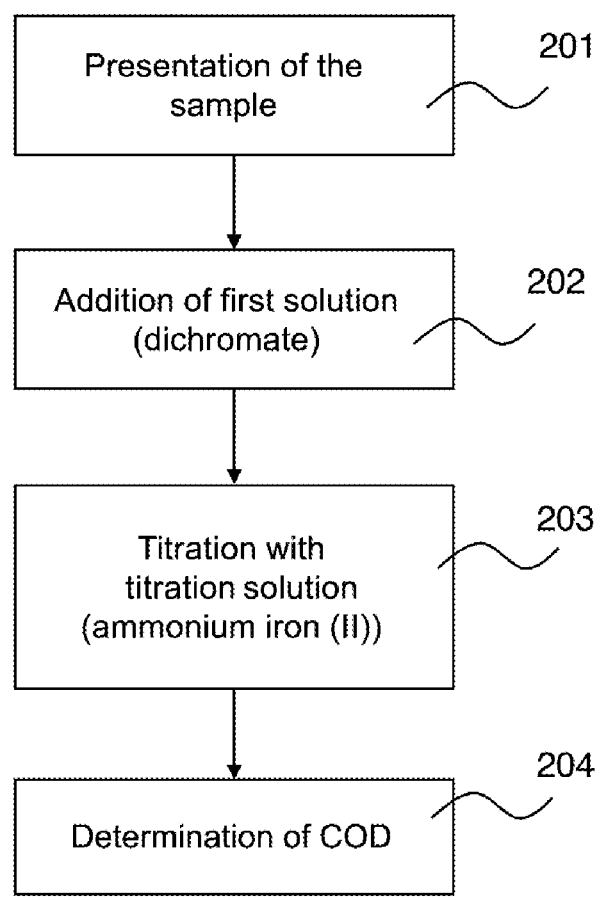
FIG. 3 shows a flow chart of a method for determining the COD of a sample liquid.

FIG. 3 schematically shows a flow chart for a method for determining the chemical oxygen demand COD of a sample liquid, for example water, by means of a redox titration, as a further embodiment. The method comprises at least four steps 201-204:

In a first step 201, the sample is presented, for example in a titration measuring cell. In the present embodiment, the presentation of the sample includes the measurement of a specific volume of the sample liquid. Furthermore, the presentation of the sample may optionally include diluting the measured volume of sample liquid. The presentation of the sample also includes acidification of the sample by addition of sulfuric acid.

In a second method step 202, the sample is heated to a temperature of 100° C. and a first solution containing dichromate is added to the sample at a slow dosing rate or in portions. Similarly to the method described with reference to FIG. 1 for the addition of permanganate solution in method step 102 described therein, measured values are also detected in the reaction mixture during the addition of the dichromate solution in the embodiment described here, with the aid of which the added volume of the dichromate solution is adjusted or regulated. The measured values can be, for example, measured values of the redox potential of the reaction mixture detected by means of a potentiometric redox sensor or an extinction or absorption of the reaction mixture. Prior to the beginning of method step 202, ferroin solution is added to the reaction mixture as a redox indicator. The measuring wavelength of the photometric measurement is correspondingly matched to the color change of ferroin.

The adjustment or regulation of the volume of the dichromate solution added to the sample in step 202 can be effected in the same way as in step 102 of the method described with reference to FIG. 1, for example by comparing the measured values with a reference value. After a predetermined total time period has been reached, above which a preferably low concentration of dichromate, which is available for the reaction, was present in the solution of the reaction mixture, method step 202 is ended.

In a third method step 203, the proportion of the added dichromate remaining in the reaction mixture is subsequently back titrated with a titration solution of ammonium iron (II). The equivalence point of titration can be detected on the basis of the measured values of the redox sensor or on the basis of measured values of a photometric sensor. In the latter case, ferroin may be added as a redox indicator, provided that it has not already been added in step 202. The equivalence point can be detected as the inflection point of the measured value curve or on the basis of exceeding or falling below a predetermined reference value of the measurand.

From the amount of ammonium iron added until the equivalence point or titration end point is reached and the known amount of dichromate added to the sample in step 202, the chemical oxygen demand of the sample can be determined in a fourth method step 204.

For carrying out the method, an apparatus is suitable which is designed to be completely analogous to the apparatus shown in FIG. 3, wherein the number of storage containers for reagents and the reagents held in the storage containers are adapted accordingly.

The method described here can be used for a plurality of other methods for quantitatively determining an analyte in a sample liquid by indirect titration, e.g. for determining the lime by acidifying the sample, expelling the resulting carbon dioxide while heating the acidified sample, and back titrating it with sodium hydroxide solution, or for determining the ammonia by acidifying the sample and back titration with sodium hydroxide solution.

The invention claimed is:

1. A quantitative titration method for determining a parameter dependent on the concentration of at least one analyte in a sample liquid, comprising:
presenting a sample of the sample liquid;
preparing a solution to be titrated from the sample, wherein the preparation comprises at least:
forming a reaction mixture by adding a volume of a first solution to the sample, wherein the first solution contains a first substance acting as a reaction partner for the at least one analyte, wherein the reaction partner enters into a chemical reaction with the at least one analyte, forming a reaction product of the at least one analyte, wherein the volume of the first solution is adjusted on the basis of measured values of a physical or chemical measurand which are detected during the addition of the first solution in the reaction mixture and whose value depends on the concentration of the at least one analyte or of the first substance in the reaction mixture;
subsequently performing a titration of the solution to be titrated from which a quantity of the first substance present in the reaction mixture after addition of the volume of the first solution is determinable; and
ascertaining a value of the parameter using the titration;
wherein during the addition of the first solution to the sample, the measured values of the physical or chemical measurand are compared with a reference value, and wherein during the addition of the first solution, time periods within which the measured values lie above the reference value or time periods within which the measured values lie below the reference value are detected and added.

2. The quantitative titration method of claim 1, wherein the addition of the first solution to the sample takes place stepwise in individual volume units or continuously with a constantly set or dynamically adjustable dosing rate.

3. The quantitative titration method of claim 1, wherein the measurand is a pH, a redox potential or an optical measurand.

4. The quantitative titration method of claim 1, wherein the performance of the titration comprises:
addition of a titration solution to the solution to be titrated, wherein said titration solution contains a second substance which enters into a chemical reaction as a titrator with a proportion of the first substance which is present as titrand in the solution to be titrated and which is not converted by the chemical reaction with the at least one analyte; and
detecting an equivalence point of titration.

5. The quantitative titration method of claim 4, wherein the value of the parameter is determined from an amount of the titrator or the titration solution added to the solution to be titrated until the equivalence point is detected.

6. The quantitative titration method of claim 1, wherein the preparation of the solution to be titrated furthermore comprises:
after addition of the volume of the first solution to the sample, addition of a volume of a second solution to the sample, wherein the second solution contains a second substance serving as a reaction partner for the first substance, the second solution entering into a chemical reaction with the first substance to form a reaction product of the first substance, and wherein the volume of the second solution is measured such that a proportion of the first substance remaining in the reaction mixture and not converted by the chemical reaction with the at least one analyte is completely converted by the second substance into the reaction product of the first substance.

7. The quantitative titration method of claim 6, wherein the performance of the titration comprises:
addition of a titration solution to the solution to be titrated, wherein said titration solution contains the first substance as a titrator, with which a proportion of the second substance present in the solution to be titrated as a titrand enters into a chemical reaction; and
detecting an equivalence point of titration.

8. The quantitative titration method of claim 7, wherein the value of the parameter is determined from an amount of the titrator or the titration solution added to the solution to be titrated until the equivalence point is detected.

9. The quantitative titration method of claim 6, wherein the parameter to be determined is a permanganate index of the sample liquid which depends on a concentration of a plurality of oxidizable analytes in the sample liquid, and wherein the first substance is permanganate, and wherein the volume of the first solution is adjusted on the basis of measured values of a measurand correlated with a concentration of permanganate during the addition of the first solution to the reaction mixture.

10. The quantitative titration method of claim 9, wherein presenting the sample comprises measuring a volume of the sample liquid and adjusting an acidic pH of the sample.

11. The quantitative titration method of claim 9, wherein the second substance is oxalate.

12. The quantitative titration method of claim 11, wherein the performance of the titration comprises:
adding a titration solution to the solution to be titrated, wherein said titration solution contains permanganate as a titrator which oxidizes oxalate present as a titrand in the solution to be titrated, and wherein the equivalence point of titration is detected by means of a photometric sensor or by means of a redox sensor.

13. The quantitative titration method of claim 1, wherein a sensor is used to detect measured values of the physical or chemical measurand during the addition of the volume of the first solution to the sample, and wherein the same sensor is used in performing the titration to detect the equivalence point of titration.

* * * * *